(12) United States Patent
Mori

(10) Patent No.: US 12,178,987 B2
(45) Date of Patent: Dec. 31, 2024

(54) MANUFACTURING METHOD FOR PACKAGED MEDICINE ADMINISTERING DEVICE

(71) Applicant: TERUMO KABUSHIKI KAISHA, Tokyo (JP)

(72) Inventor: Kimiya Mori, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/474,478

(22) Filed: Sep. 26, 2023

(65) Prior Publication Data

US 2024/0009380 A1 Jan. 11, 2024

Related U.S. Application Data

(63) Continuation of application No. PCT/JP2022/010746, filed on Mar. 10, 2022.

(30) Foreign Application Priority Data

Mar. 26, 2021 (JP) .................................. 2021-053987

(51) Int. Cl.
*A61M 5/00* (2006.01)
*A61M 5/315* (2006.01)
(Continued)

(52) U.S. Cl.
CPC ............ *A61M 5/002* (2013.01); *A61M 5/001* (2013.01); *A61M 5/31513* (2013.01); *A61M 5/3202* (2013.01); *B65B 55/02* (2013.01)

(58) Field of Classification Search
CPC ......... B65B 55/02; B65B 55/10; B65B 55/18; B65B 2210/06; A61M 2005/3117; A61M 2209/06
(Continued)

(56) References Cited

U.S. PATENT DOCUMENTS 3,406,686 A 10/1968 Keller
10,046,156 B2 * 8/2018 Gardner ................. A61B 50/30
(Continued)

FOREIGN PATENT DOCUMENTS

EP  2 918 301 A1  9/2015
EP  3 380 165 A1  10/2018
(Continued)

OTHER PUBLICATIONS

International Search Report issued in the corresponding International Patent Application No. PCT/JP2022/010746, dated Apr. 26, 2022.
(Continued)

*Primary Examiner* — Valentin Neacsu
(74) *Attorney, Agent, or Firm* — Foley & Lardner LLP

(57) ABSTRACT

A manufacturing method for a packaged medicine administration device that includes a medicine administration device including an outer tube filled with a medicine, and a puncture device for medicine administration; a cylindrical case encapsulating and holding the medicine administration device; and a package accommodating the cylindrical case-encapsulated medicine administration device encapsulated and held by the cylindrical case, the package being sealed, the manufacturing method including: a step of preparing the cylindrical case-encapsulated medicine administration device; a step of adding hydrogen peroxide to a site to be located on an inner side of the cylindrical case; a step of accommodating the cylindrical case-encapsulated medicine administration device in the package; a step of sealing the package; and a step of sterilizing the cylindrical case-encapsulated medicine administration device with a hydrogen peroxide atmosphere formed by the added hydrogen peroxide in a state in which the package is sealed.

8 Claims, 8 Drawing Sheets

(51) Int. Cl.
*A61M 5/32* (2006.01)
*B65B 55/02* (2006.01)
(58) Field of Classification Search
USPC .................................. 53/431, 425; 604/199
See application file for complete search history.

(56) References Cited

U.S. PATENT DOCUMENTS

| | | | | |
|---|---|---|---|---|
| 10,806,850 | B2* | 10/2020 | Patel | A61M 5/001 |
| 2015/0174338 | A1* | 6/2015 | Takemoto | A61M 5/003 |
| | | | | 206/364 |
| 2015/0258282 | A1* | 9/2015 | Imai | A61M 5/3272 |
| | | | | 604/272 |
| 2016/0220762 | A1* | 8/2016 | Goral | A61M 5/422 |
| 2018/0221564 | A1* | 8/2018 | Patel | B65B 55/06 |
| 2018/0369498 | A1* | 12/2018 | Schader | A61M 5/3204 |
| 2020/0078533 | A1* | 3/2020 | Modi | A61M 5/50 |
| 2020/0246533 | A1* | 8/2020 | Patel | A61L 2/081 |
| 2022/0133981 | A1* | 5/2022 | Dumont | A61M 5/31505 |
| | | | | 206/364 |
| 2024/0009380 | A1* | 1/2024 | Mori | A61M 5/001 |

FOREIGN PATENT DOCUMENTS

| | | |
|---|---|---|
| JP | H11-155948 A | 6/1999 |
| JP | 2004-275616 A | 10/2004 |
| JP | 2006-016053 A | 1/2006 |
| JP | 2015-171407 A | 10/2015 |
| JP | 2018-535042 A | 11/2018 |
| JP | 2020-069105 A | 5/2020 |
| JP | 2021-159184 A | 10/2021 |
| WO | WO-2017/089275 A1 | 6/2017 |
| WO | WO-2020/078920 A1 | 4/2020 |

OTHER PUBLICATIONS

Written Opinion of the International Searching Authority issued in the corresponding International Patent Application No. PCT/JP2022/010746, dated Apr. 26, 2022.
Extended European Search Report issued in EP Appl. No. 22775174.0 dated Jul. 24, 2024.

* cited by examiner

MANUFACTURING METHOD FOR PACKAGED MEDICINE ADMINISTERING DEVICE

CROSS REFERENCE TO RELATED APPLICATIONS

This application is a bypass continuation of PCT Application No. PCT/JP2022/010746, filed on Mar. 10, 2022, which claims priority to Japanese Application No. JP2021-053987, filed on Mar. 26, 2021. The entire contents of these applications are incorporated by reference herein.

BACKGROUND

The present disclosure relates to a manufacturing method for a packaged medicine administration device, and particularly to a manufacturing method for a packaged medicine administration device in which an accommodated medicine administration device is in a sterilized state.

An injector (syringe with an injection needle) has been used to administer a drug solution to a patient. As a method for accommodating a drug solution to be administered to a patient in a syringe, for example, there is a method of sucking out a drug solution from an ampoule or a vial storing the drug solution. The ampoule is obtained by charging the drug solution and then melting an end of a container with heat to seal the container. When the drug solution is used, it is necessary to fold a neck of the container and insert an injection needle from the folded part to suck out the drug solution. The vial is obtained by plugging a container (bottle) containing the drug solution with rubber. When the drug solution is used, it is necessary to insert an injection needle into the rubber plug to suck out the drug solution.

On the other hand, there is a prefilled syringe in which a syringe is stored in the state of being filled with a drug solution in advance. In the prefilled syringe, it is unnecessary to suck out the drug solution from a container in which the drug solution is stored before administration of the drug solution.

JP 2018-535042 A (Patent Literature 1) (US 2018-369498 A, EP 3380165, WO 2017-089275) discloses a medicament injection device capable of providing an automated mechanism for inserting a needle into a medicament cartridge and reducing the amount of handling of the needle by a user prior to injection.

In addition, an applicant of the present application proposed a liquid administration device disclosed in JP 2015-171407 A (Patent Literature 2) (US 2015-258282 A, EP 2918301).

SUMMARY

In Patent Literature 1, provided are: a medicament cartridge holder fixed to a main body and configured to hold the medicament cartridge; a needle carrier that supports the needle and is axially movable with respect to the main body; and a rotatable cap at a distal end of the device, the cap including a first pre-stressed spring coupled to the needle carrier. The cap is arranged so that rotational movement thereof causes release of the first pre-stressed spring thereby causing the needle carrier to move axially towards a proximal end of the device. In such a medicament injection device, preparation for administration is easy.

A liquid administration device 10 of Patent Literature 2 includes: a structure 40 including a syringe 60 capable of storing liquid therein and a needle tube 66 capable of communicating with the inside of the syringe 60; an operation unit 20 that discharges the liquid inside the syringe 60 from the needle tube 66 by moving toward the structure 40 in a distal direction; a cover member 30 that is movable between a protection position at which the needle tube 66 is covered and an exposure position at which the needle tube 66 is exposed; a second coil spring 11 that biases the cover member 30 in the distal direction; and a first coil spring 12 that biases the operation unit 20 toward the structure 40 in the distal direction, and the operation unit 20 and the structure 40 have resistance projection portions 96 and resistance claw portions 105 that apply a pressing force to each other while changing a contact position when the operation unit 20 moves to the structure 40 in the distal direction.

However, the medicament injection device of Patent Literature 1 and the liquid administration device of Patent Literature 2 are constituted by many members, and are difficult to assemble in a sterile state. The needle in the medicament injection device of Patent Literature 1 is encapsulated with a cap, but is not packaged in the sterile state. In addition, medical tools as described above are easy to prepare for administration and perform an administration operation, and thus, are assumed to be used in a highly microbially controlled atmosphere such as an operating room or an ICU.

Therefore, the present disclosure provides a manufacturing method for a packaged medicine administration device constituted by a plurality of members, the manufacturing method for the packaged medicine administration device in which the entire medicine administration device including a needle part for puncture in a package has been sterilized and can be kept in such a state.

According to one embodiment, a manufacturing method for a packaged medicine administration device includes: a medicine administration device including an outer tube filled with a medicine and a puncture device for medicine administration; a cylindrical case encapsulating and holding the medicine administration device; and a package accommodating the cylindrical case-encapsulated medicine administration device encapsulated and held by the cylindrical case and being sealed, the manufacturing method including: a step of preparing the cylindrical case-encapsulated medicine administration device; a step of adding hydrogen peroxide to a site to be located on an inner side of the cylindrical case of the cylindrical case-encapsulated medicine administration device; a step of accommodating the cylindrical case-encapsulated medicine administration device in the package; a step of sealing the package accommodating the cylindrical case-encapsulated medicine administration device; and a package sealing and post-storage step of sterilizing the cylindrical case-encapsulated medicine administration device with an hydrogen peroxide atmosphere formed by the added hydrogen peroxide in a state in which the package is sealed.

DETAILED DESCRIPTION

Figure 1:
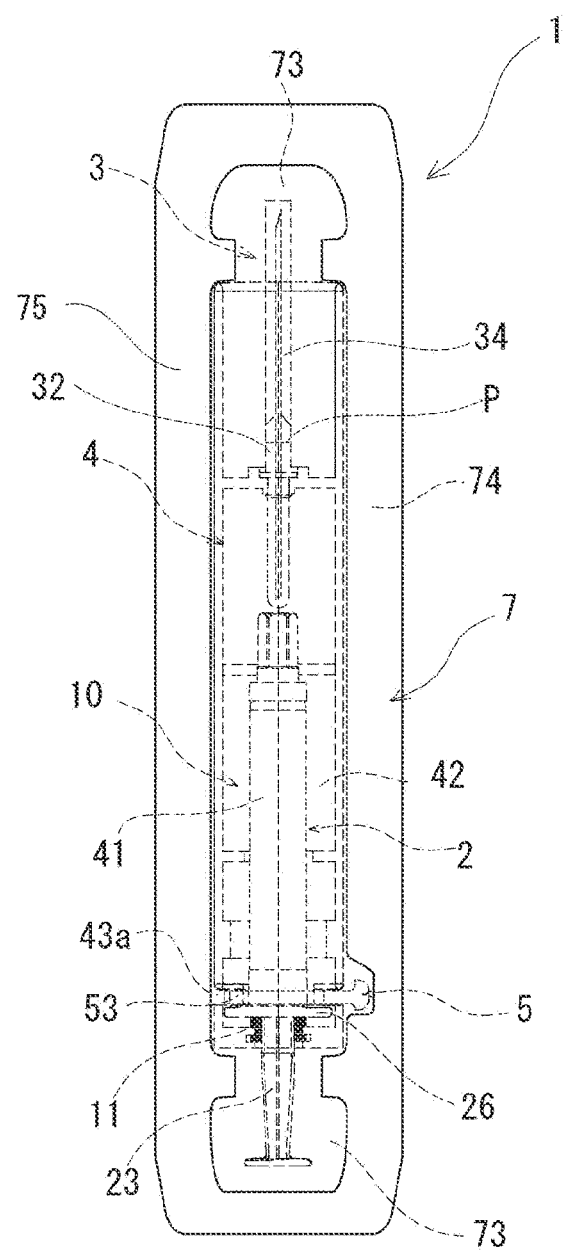
FIG. 1 is an explanatory view for describing a manufacturing method for a packaged medicine administration device according to an embodiment of the present invention.

A manufacturing method for a packaged medicine administration device of the present disclosure will be described with reference to the drawings.

As illustrated in FIGS. 1 to 6, a manufacturing method for a packaged medicine administration device 1 of the present embodiment is a manufacturing method for a packaged medicine administration device including: a medicine administration device including an outer tube 21 filled with a medicine 25 and a puncture device 3 for medicine administration; a cylindrical case 4 encapsulating and holding the medicine administration device; and a sealed package 7 that accommodates a cylindrical case-encapsulated medicine administration device encapsulated and held by the cylindrical case 4.

The manufacturing method for the packaged medicine administration device of the present embodiment includes: a step of preparing the cylindrical case-encapsulated medicine administration device 10; a step of adding hydrogen peroxide to a site to be located on the inner side of the cylindrical case 4 of the cylindrical case-encapsulated medicine administration device 10; a step of accommodating the cylindrical case-encapsulated medicine administration device 10 in the package 7; a step of sealing the package 7 accommodating the cylindrical case-encapsulated medicine administration device 10; and a package sealing and post-storage step of sterilizing the cylindrical case-encapsulated medicine administration device 10 with a hydrogen peroxide atmosphere formed by the added hydrogen peroxide in a state in which the package 7 is sealed.

Therefore, in the package sealing and post-storage step, the package is filled with a hydrogen peroxide gas due to the added hydrogen peroxide, and the inside and an outer surface of the cylindrical case-encapsulated medicine administration device are sterilized by the filling hydrogen peroxide gas. Further, because the package is already packaged, a sterile state is maintained until the package is opened after the package sealing and post-storage step, and thus, it is possible to use the package in a highly microbially controlled atmosphere such as an operating room or an ICU.

The cylindrical case-encapsulated medicine administration device 10 to which the present embodiment is applied includes the cylindrical case 4 and the medicine administration device encapsulated and held by the cylindrical case 4.

Further, as the medicine administration device, one including at least the outer tube filled with the medicine and a puncture needle for medicine administration is used. For example, as the medicine administration device as illustrated in FIGS. 1 to 6, provided are: the puncture device 3 that includes a hollow cylindrical member 31 having a puncture needle portion on one end side and a connection needle portion on the other end side, a hub 32 mounted between the puncture needle portion and the connection needle portion of the hollow cylindrical member, and a puncture needle portion cap 34 mounted on the puncture needle portion side of the hub; and a prefilled syringe 2 that includes an outer tube, a gasket slidably accommodated in the outer tube, a distal end sealing member that seals a distal end of the outer tube and can be pierced by the connection needle portion, the medicine 25 charged in the outer tube, and a plunger pressing the gasket.

The cylindrical case-encapsulated medicine administration device 10 used in this embodiment includes: the puncture device 3, the prefilled syringe 2, the cylindrical case 4 that accommodates the both such that a distal end portion of a connection needle portion 31b of the puncture device 3 and a distal end of the prefilled syringe 2 face each other, and a stopper 5.

Figure 4:
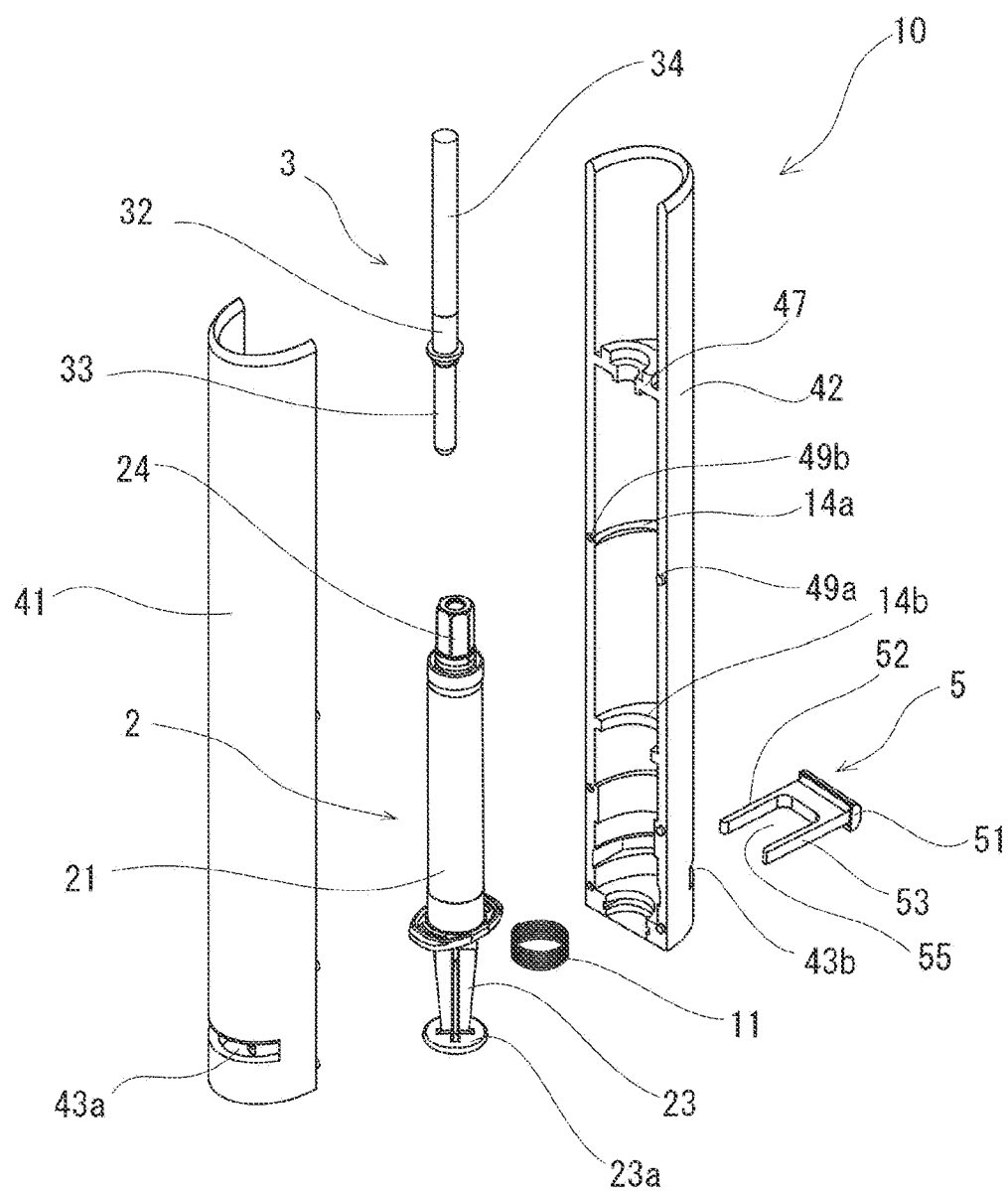
FIG. 4 is an explanatory view of constituent members of the cylindrical case-encapsulated medicine administration device illustrated in FIG. 3.
Figure 5:
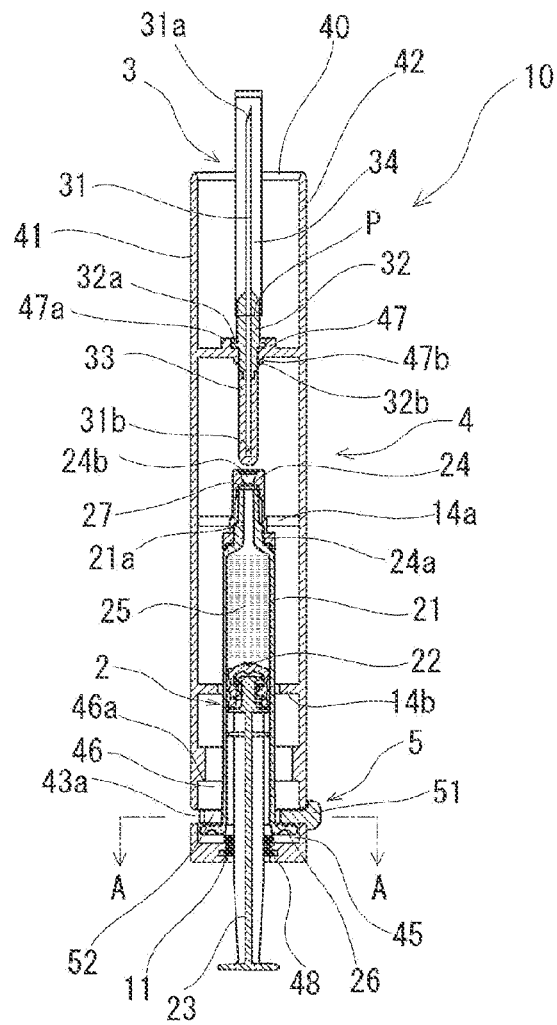
FIG. 5 is a longitudinal cross-sectional view of the cylindrical case-encapsulated medicine administration device illustrated in FIG. 3.

As illustrated in FIGS. 4 and 5, the puncture device 3 includes: the hollow cylindrical member 31 having a puncture needle portion 31a and the connection needle portion 31b; the hub 32 mounted between the puncture needle portion 31a and the connection needle portion 31b of the hollow cylindrical member 31; an elastic sleeve 33 that has one end being mounted to the hub 32 and a close rear end and encapsulates the connection needle portion 31b; and the puncture needle portion cap 34 that has a rear end being mounted to the hub 32 and a closed distal end and encapsulates the puncture needle portion 31a.

In addition, a distal end opening of the puncture needle portion 31a is an opening having a blade surface, and a rear end opening of the connection needle portion 31b is also an opening having a blade surface, thereby forming a so-called double-ended needle. The elastic sleeve 33 is elastically deformed by being pressed toward the hub 32 and can be pierced by the connection needle portion 31b, and the connection needle portion 31b protrudes by piercing through the sleeve 33.

The prefilled syringe 2 includes: the outer tube 21 having an outer surface protruding portion 26 at a rear end portion; a sealing member 24 that seals a distal end portion of the outer tube 21 and can be pierced by the connection needle portion 31b of the puncture device 3; and a gasket 22 slidable inside the outer tube 21 in a liquid-tight state.

Further, in the cylindrical case-encapsulated medicine administration device 10, the cylindrical case 4 accommodates the puncture device 3 such that the puncture device 3 is not movable and the distal end portion of the puncture needle portion 31a protrudes, accommodates the prefilled syringe 2 in the cylindrical case 4 so as to be movable toward the puncture device 3, and further includes side portion openings 43a and 43b provided at a rear end portion.

The cylindrical case-encapsulated medicine administration device 10 includes: a biasing member 11 that abuts on the outer tube 21 and biases the prefilled syringe 2 toward the connection needle portion 31b; and the stopper 5 that is detachably inserted into the side portion openings 43a and 43b of the cylindrical case 4, abuts on the outer surface protruding portion 26 of the outer tube 21, and restricts the prefilled syringe 2 from moving toward the puncture device 3. The cylindrical case-encapsulated medicine administration device 10 is configured such that the prefilled syringe 2 moves toward the puncture device 3 by being pressed by the biasing member 11 after the stopper 5 is detached, and the sealing member 24 of the prefilled syringe 2 is penetrated by the connection needle portion 31*b*.

In other words, the biasing member 11 presses the prefilled syringe such that the sealing member 24 of the prefilled syringe 2 is pierced by the connection needle portion 31*b* of the puncture device 3 after the stopper 5 is detached.

The prefilled syringe 2 includes: the outer tube 21; the sealing member (seal cap) 24 attached to a nozzle portion of the outer tube 21; the gasket 22 slidably accommodated in the outer tube; and a plunger 23 attached to the gasket 22.

The outer tube 21 is a cylindrical body made of a transparent or translucent material, preferably a material having low permeability to oxygen, water vapor, particularly the hydrogen peroxide gas. The outer tube 21 includes an outer tube main body portion and a nozzle portion 21*a* provided on a distal end side of the outer tube main body portion. The nozzle portion 21*a* is located at a distal end of the outer tube 21, has an opening for discharging a drug solution or the like in the outer tube at a distal end, and is formed to be reduced in diameter in a tapered shape toward the distal end. The nozzle portion 21*a* includes a sealing member mounting portion.

As illustrated in FIGS. 4 and 5, the sealing member 24 includes a cylindrical sealing member main body and a seal member 27 accommodated in the sealing member main body. The sealing member 24 includes a nozzle portion accommodating portion and a sealing member-side outer tube mounting portion 24*a*. In this embodiment, the cylindrical sealing member main body is a cylindrical member that is opened on one end side and the other end side, and includes an opening 24*b*, which is expanded in diameter in a tapered shape and is adapted for mounting of the connection needle portion 31*b*, on the distal end side. Further, the seal member 27 is accommodated behind the opening 24*b*. One end of the seal cap is closed by the seal member 27.

The seal member 27 is adapted to liquid-tightly seal the distal end opening of the nozzle portion. The nozzle portion 21*a* is sealed in a liquid-tight manner as the distal end opening of the nozzle portion abuts on the seal member 27. In addition, the seal member 27 is made of an elastic material that can be pierced by the connection needle portion 31*b*. In addition, preferably, the seal member 27 is made of an elastic material and is poorly permeable to hydrogen peroxide.

As illustrated in FIG. 5, the gasket 22 includes a main body portion extending with substantially the same outer diameter and a plurality of annular ribs provided on the main body portion, and these ribs contact an inner surface of the outer tube 21 in a liquid-tight manner.

As materials for forming the gasket 22, rubbers having elasticity (for example, butyl rubber, latex rubber, silicone rubber, and the like), synthetic resins (for example, styrene-based elastomers such as an SBS elastomer and an SEBS elastomer, and olefin-based elastomers such as an ethylene-α-olefin copolymer elastomer), and the like can be used. In addition, the gasket 22 is preferably poorly permeable to hydrogen peroxide.

In the cylindrical case-encapsulated medicine administration device 10 of this embodiment, the gasket 22 includes the plunger 23 whose rear portion protrudes from the cylindrical case. The plunger 23 includes a protruding portion protruding in a cylindrical shape at a distal end portion, and a male screw is formed on an outer surface of the protruding portion. In addition, the plunger 23 includes a shaft portion extending axially to have a cruciform cross-sectional shape, a pressing disk portion provided at a rear end portion, and a rib provided in the middle of the shaft portion.

The prefilled syringe 2 is filled with the medicine (drug solution) 25. As the medicine (drug solution) 25, emergency administration medicines such as an adrenaline injection solution preparation (vasoconstrictor), which is a drug for anaphylactic shock, an antiarrhythmic agent (for example, lidocaine), an anticholinergic agent (for example, atropine), an anticonvulsant (for example, diazepam), a rocuronium bromide injection solution preparation, nitroglycerin, and physiological saline, drug solutions such as cyclosporine, benzodiazepine medicines, a high-concentration sodium chloride injection solution, vitamins, minerals, and antibiotics, vitamin agents (multivitamin agents), various amino acids, antithrombotic agents such as heparin, insulin, antitumor agents, analgesics, cardiotonic agents, Intravenous anesthetics, antiparkinsonian agents, ulcer therapeutic agents, adrenocortical hormone agents, antiarrhythmic agent, correcting electrolytes, antiviral agents, immunostimulants, and the like are conceivable.

As illustrated in FIGS. 3 to 6, the cylindrical case 4 is formed of a coupler of a first case member 41 and a second case member 42, and is an elliptical-cylindrical body.

Figure 3:
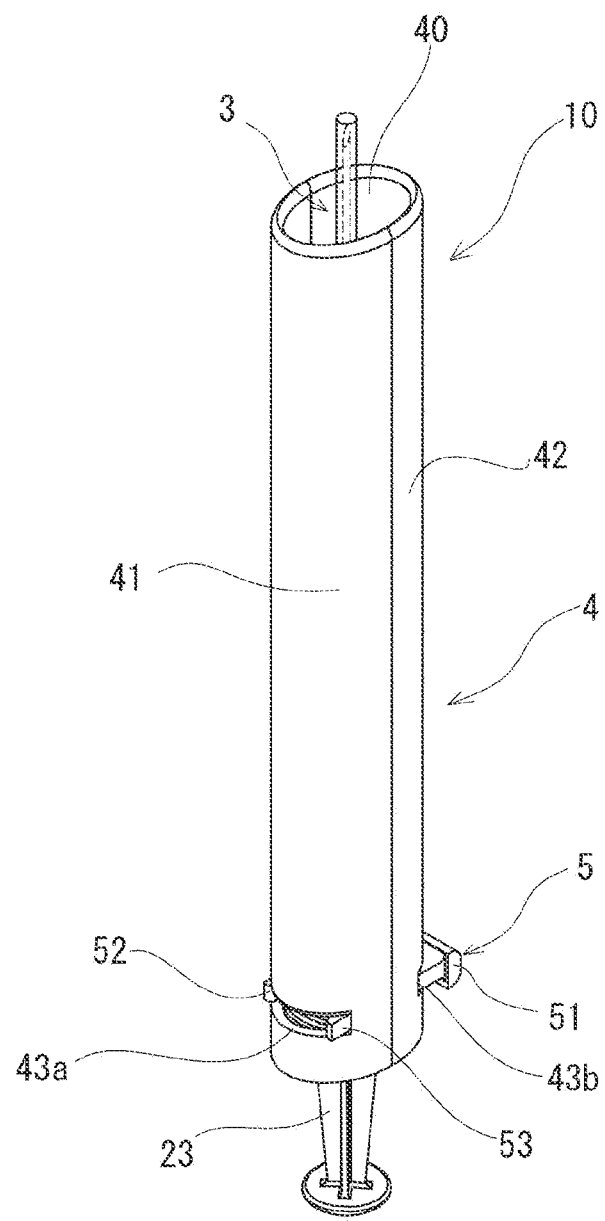
FIG. 3 is a perspective view of a cylindrical case-encapsulated medicine administration device used in the manufacturing method for the packaged medicine administration device illustrated in FIGS. 1 and 2.

The first case member 41 and the second case member 42 are semi-cylindrical members, include a plurality of protrusions 49*a* and a recess 49*b* at an inner peripheral edge portion serving as an abutment portion, and form the coupler as the both engage with each other as illustrated in FIG. 3.

The cylindrical case 4 has the elliptical-cylindrical shape capable of accommodating the outer surface protruding portion 26 of the prefilled syringe 2. The cylindrical case 4 includes a prefilled syringe accommodating portion therein, and includes a hollow cylindrical member mounting portion 47 protruding inward from an inner surface, and guide portions 14*a* and 14*b* that can come into contact with an outer surface of the outer tube 21 of the prefilled syringe 2 and guide sliding of the prefilled syringe 2. The guide portions 14*a* and 14*b* are preferably formed to protrude inward from the inner surface of the cylindrical case 4 at positions corresponding to a cylindrical main body of the accommodated prefilled syringe 2 and formed to have an internal shape slightly larger than an external shape of the prefilled syringe 2.

The cylindrical case 4 includes engagement portions with the stopper 5 to be described later. In this embodiment, the engagement portions with the stopper 5 in the cylindrical case are formed by the two side portion openings (through openings) 43*a* and 43*b* formed to face each other. Note that the engagement portion with the stopper 5 may be formed by providing one side portion opening and a recess provided at a position facing the side portion opening and capable of engaging with the stopper (one end portion), or formed by providing only one side portion opening and an inner surface rib, which is capable of engaging with the stopper (one end portion) and does not hinder movement of the prefilled syringe, on the inner surface of the cylindrical case facing the side portion opening and located slightly on the distal end side.

The cylindrical case 4 includes: a first accommodating portion 45 that stores the outer surface protruding portion 26 of the prefilled syringe, the biasing member 11 in a compressed state, and the stopper 5 in a state in which the prefilled syringe is locked by the stopper 5; and a second accommodating portion 46 that stores the outer surface protruding portion 26 of the prefilled syringe after the stopper 5 is detached and then the prefilled syringe moves forward. In addition, a part of the stretched biasing member on the distal end side is accommodated in the second accommodating portion.

In addition, the cylindrical case 4 includes a movement restricting abutment portion 46*a* that abuts on a distal end surface of the outer surface protruding portion 26 of the prefilled syringe 2 after the stopper 5 is detached and then the sealing member 24 of the prefilled syringe 2 is pierced by the connection needle portion 31*b* of the puncture device 3. In this embodiment, the movement restricting abutment portion 46*a* is formed by a distal end surface of the second accommodating portion 46.

In addition, as illustrated in FIGS. 4 and 5, the cylindrical case 4 includes the side portion openings (through openings) 43*a* and 43*b* having a slit shape and provided at the rear end portion. The stopper 5 is inserted so as to penetrate the side portion openings (through openings) 43*a* and 43*b*. The stopper 5 can be removed. Further, a rear surface of the stopper 5 abuts on a front surface of the outer surface protruding portion 26 of the prefilled syringe 2 to restrict the prefilled syringe 2 from moving forward.

It is preferable that the cylindrical case 4 has transparency or translucency through which the stored puncture device 3 and the prefilled syringe 2 can be visually recognized. In addition, as illustrated in FIG. 5, the biasing member 11 accommodated in the first accommodating portion 45 of the cylindrical case 4 is compressed between a rear end portion 48 of the cylindrical case 4 and a rear surface of the outer surface protruding portion 26 of the prefilled syringe 2. In this embodiment, a coil spring is used as the biasing member 11, and the plunger 23 of the prefilled syringe 2 penetrates the biasing member 11. In addition, a rear end portion of the biasing member 11 is accommodated and fixed in an annular recess provided at the rear end portion of the cylindrical case 4 in this embodiment.

Figure 6:
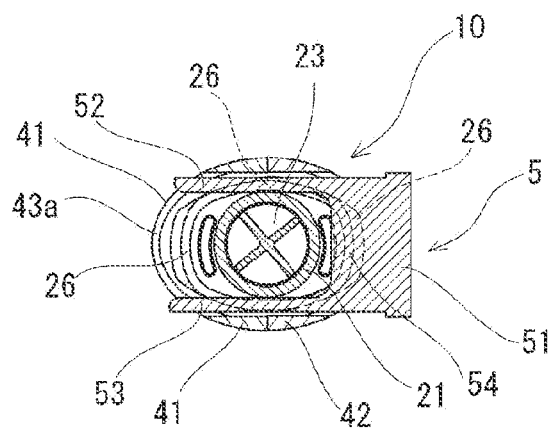
FIG. 6 is a cross-sectional view taken along line A-A of FIG. 5.

As illustrated in FIGS. 4 to 6, the stopper 5 includes a base portion 54, two extension portions 52 and 53 extending forward from the base portion 54 and facing each other, a notch portion 55, which is formed between the two extension portions 52 and 53 and the base portion 54 to allow the main body portion of the outer tube 21 to penetrate therethrough, and a grip portion 51 provided behind the base portion 54.

The cylindrical case 4 includes the engagement portions with the two extension portions 52 and 53, and when the stopper 5 is mounted to the cylindrical case 4, the base portion 54 engages with the one side portion opening 43*b* of the cylindrical case 4, and distal end portions of the two extension portions 52 and 53 engage with the engagement portions of the cylindrical case 4. In addition, a proximal end portion of the base portion 54 protrudes from the side portion openings of the cylindrical case.

Specifically, the grip portion 51 is a bulging portion. In this embodiment, the stopper 5 has a U-shaped form, penetrates the cylindrical case 4, sandwiches the outer tube 21 of the prefilled syringe 2 on the inner side of the U shape, and is inserted so as to penetrate the two side portion openings, thereby suppressing an axial movement of the prefilled syringe.

As illustrated in FIGS. 3 and 6, when the stopper 5 is mounted to the cylindrical case 4, the grip portion 51 protrudes from the opening 43*b*, which is one of the side portion openings (through openings) of the cylindrical case 4, and the distal end portions of the two extension portions 52 and 53 protrude from the opening 43*a*, which is one of the side portion openings (through openings). In addition, as illustrated in FIGS. 5 and 6, lower surfaces of the base portion 54 and the two extension portions 52 and 53 of the stopper 5 abut on an upper surface of the outer surface protruding portion 26 of the prefilled syringe 2, an upper surface of the base portion 54 of the stopper 5 abuts on an upper edge portion of the one opening 43*b* of the cylindrical case 4, and upper surfaces of the two extension portions 52 and 53 abut on an upper edge portion of the other opening 43*a* of the cylindrical case 4. As a result, the stopper 5 is sandwiched between the upper edge portions of the openings 43*a* and 43*b* of the cylindrical case 4 and the outer surface protruding portion 26 of the prefilled syringe 2 in the side portion openings (through openings) of the cylindrical case 4, and is not easily detached.

Figure 7:
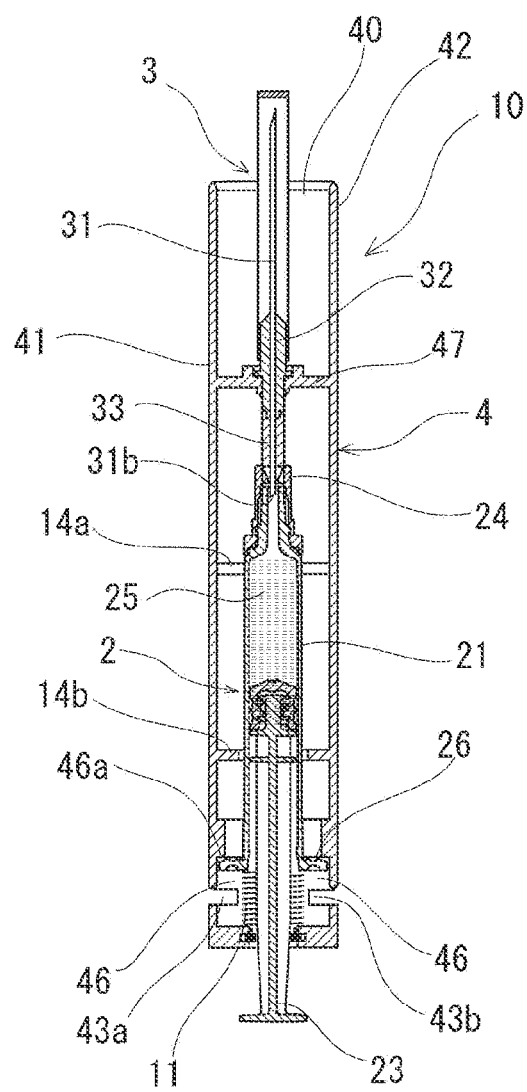
FIG. 7 is an explanatory view for describing an action of the cylindrical case-encapsulated medicine administration device illustrated in FIG. 3.

Further, in the cylindrical case-encapsulated medicine administration device 10 of the present embodiment, the locked state of the outer surface protruding portion 26 of the prefilled syringe 2 by the stopper 5 is released when the stopper 5 is detached (removed) from the cylindrical case-encapsulated medicine administration device 10 as illustrated in FIG. 7. As a result, the outer surface protruding portion 26 of the prefilled syringe 2 is pressed from the rear by the biasing member 11 and moves forward (toward the puncture device 3).

Further, the prefilled syringe 2 (specifically, the sealing member 24) and the puncture device 3 of this embodiment are accommodated in the cylindrical case 4 such that central axes thereof are substantially the same. Furthermore, even when the prefilled syringe 2 is moved by the above-described pressing of the biasing member 11, the central axis of the prefilled syringe 2 (specifically, the sealing member 24) and the central axis of the puncture device 3 slide forward (toward the puncture device 3) while maintaining substantially the same state by the guide portions 14*a* and 14*b* and the like.

A biasing force of the prefilled syringe 2 by the biasing member 11 at least presses the prefilled syringe such that the seal member 27 of the sealing member 24 of the prefilled syringe 2 is pierced by the connection needle portion 31*b* of the puncture device 3 after the stopper 5 is detached. In addition, the biasing force of the prefilled syringe 2 by the biasing member 11 enables the prefilled syringe 2 to move forward (toward the puncture device 3) until the outer surface protruding portion 26 of the prefilled syringe 2 abuts on the movement restricting abutment portion 46*a* of the second accommodating portion 46 of the cylindrical case 4, and further presses the prefilled syringe 2 after the outer surface protruding portion 26 of the prefilled syringe 2 abuts on the movement restricting abutment portion 46*a* of the second accommodating portion 46 of the cylindrical case 4.

Further, the seal member 27 of the sealing member 24 of the prefilled syringe 2 having moved forward is pierced by the connection needle portion 31*b* of the puncture device 3 as illustrated in FIG. 7. As a result, the inside of the hollow cylindrical member 31 of the puncture device 3 communicates with the inside of the prefilled syringe 2. In the communicating state, a part of the plunger 23 on a rear portion side including a pressing operation portion 23*a* protrudes from the cylindrical case 4 by a predetermined length.

Further, the cap 34 of the puncture device 3 is removed so that medicine administration preparation is completed. In addition, the plunger 23 can be pressed until the pressing operation portion 23*a* abuts on a rear end surface of the cylindrical case 4, and can discharge the medicine by the amount of movement of the plunger 23.

Then, the manufacturing method for the packaged medicine administration device of the present embodiment includes: a step of preparing the cylindrical case-encapsulated medicine administration device 10; a step of adding hydrogen peroxide to a site to be located on the inner side of the cylindrical case 4 of the cylindrical case-encapsulated medicine administration device 10; a step of accommodating the cylindrical case-encapsulated medicine administration device 10 in the package 7; a step of sealing the package 7 accommodating the cylindrical case-encapsulated medicine administration device 10; and a package sealing and post-storage step of sterilizing the cylindrical case-encapsulated medicine administration device 10 with a hydrogen peroxide atmosphere formed by the added hydrogen peroxide in a state in which the package 7 is sealed.

In the step of preparing the cylindrical case-encapsulated medicine administration device 10, the above-described cylindrical case-encapsulated medicine administration device 10 is prepared. Specifically, the puncture device 3, the aseptically filled prefilled syringe 2, the cylindrical case 4 that accommodates the both such that a distal end portion of the connection needle portion 31b of the puncture device 3 and the distal end of the prefilled syringe 2 face each other, the stopper 5, and the biasing member 11 as illustrated in FIG. 4 are prepared, and assembled into the state illustrated in FIGS. 3 and 5. The cylindrical case-encapsulated medicine administration device 10 can administer the medicine in the state of being encapsulated in the cylindrical case 4 after the prefilled syringe 2 and the puncture device 3 are connected at the time of use.

Next, the step of adding the hydrogen peroxide to the site to be located on the inner side of the cylindrical case 4 of the cylindrical case-encapsulated medicine administration device 10 is performed.

It is assumed that the cylindrical case-encapsulated medicine administration device 10 is used for emergency adrenaline injection when anaphylactic shock due to a medicine or the like occurs in an operating room or the like, for example. Therefore, it is necessary to maintain the sterilization of the entire cylindrical case-encapsulated medicine administration device 10 until the package is opened.

In the cylindrical case-encapsulated medicine administration device 10, the puncture device 3 is of a type including a so-called double-ended needle, the puncture needle portion 31a is encapsulated by the cap 34, and the connection needle portion 31b is encapsulated by the elastic sleeve 33. As a result of intensive studies by the inventors of the present application, it has been confirmed that it is not easy to reliably sterilize inner surfaces of the puncture needle portion 31a and the cap 34 by a test in which a biological indicator was installed in the cap and sterilization with a hydrogen peroxide atmosphere was performed. Note that it has been found that this is because flow of a sterilization gas is not sufficient because the cap 34 is fitted to the hub with a gap therebetween, but the gap is small.

Note that the cylindrical case-encapsulated medicine administration device 10 has a large number of components and requires assembly work, and it is difficult to aseptically perform the assembly and packaging. In addition, the prefilled syringe is filled with the medicine, and thus, it is also difficult to perform electron beam sterilization and radiation sterilization after the assembly and packaging.

In view of the above circumstances, it has been found that the addition of the hydrogen peroxide (hydrogen peroxide solution) in the step of adding the hydrogen peroxide is preferably performed by adding (for example, dropping) the hydrogen peroxide (hydrogen peroxide solution) to the inner side of the cylindrical case 4 of the cylindrical case-encapsulated medicine administration device 10, particularly, to a portion (P) between the puncture needle portion cap 34 (specifically, a rear end portion of the puncture needle portion cap 34) and the hub 32. Furthermore, the addition of the hydrogen peroxide (hydrogen peroxide solution) may also be performed with respect to another site in addition to the above site, and in this case, is preferably performed with respect to the plunger, for example, a side surface of the shaft portion of the plunger. The addition of the hydrogen peroxide (hydrogen peroxide solution) to the plunger is preferably performed with respect to a site located in the cylindrical case 4, but may be performed to a site exposed from the cylindrical case 4. In particular, it is preferable to perform the addition with respect to the side surface of the shaft portion of the plunger located in the cylindrical case 4.

The step of adding the hydrogen peroxide is preferably performed by adding the hydrogen peroxide (hydrogen peroxide solution) to a portion (P) between the puncture needle portion cap 34 and the hub 32 in the cylindrical case-encapsulated medicine administration device 10 after the above-described step of preparing the cylindrical case-encapsulated medicine administration device 10.

Note that the step of adding the hydrogen peroxide may be performed in parallel with the above-described step of preparing the cylindrical case-encapsulated medicine administration device 10. For example, the prefilled syringe 2 may be mounted in the cylindrical case 4, and the puncture device 3 in which the hydrogen peroxide has been added to the portion (P) between the puncture needle portion cap 34 and the hub 32 may be mounted in the cylindrical case 4. Furthermore, when the hydrogen peroxide is added to the plunger 23 of the prefilled syringe 2, the addition may be performed before or after mounting the prefilled syringe 2 in the cylindrical case 4, or after assembling the cylindrical case-encapsulated medicine administration device 10.

Next, the step of accommodating the cylindrical case-encapsulated medicine administration device 10 in the package 7 is performed.

This step is performed by arranging the cylindrical case-encapsulated medicine administration device 10 in the package 7. Note that either this accommodation step or the above-described step of adding the hydrogen peroxide may be performed first. When the accommodation step is performed first, the above-described step of adding the hydrogen peroxide is performed before sealing the package after the cylindrical case-encapsulated medicine administration device 10 is arranged in the package 7. In addition, when the accommodation step is performed later, the accommodation step is performed by arranging the cylindrical case-encapsulated medicine administration device 10 to which the hydrogen peroxide has been added in the package 7.

The package 7 that is poorly permeable to hydrogen peroxide may be used, but it is preferable to prepare a hydrogen peroxide permeation amount adjustment functional package that allows and restricts permeation caused by diffusion of hydrogen peroxide.

Figure 2:
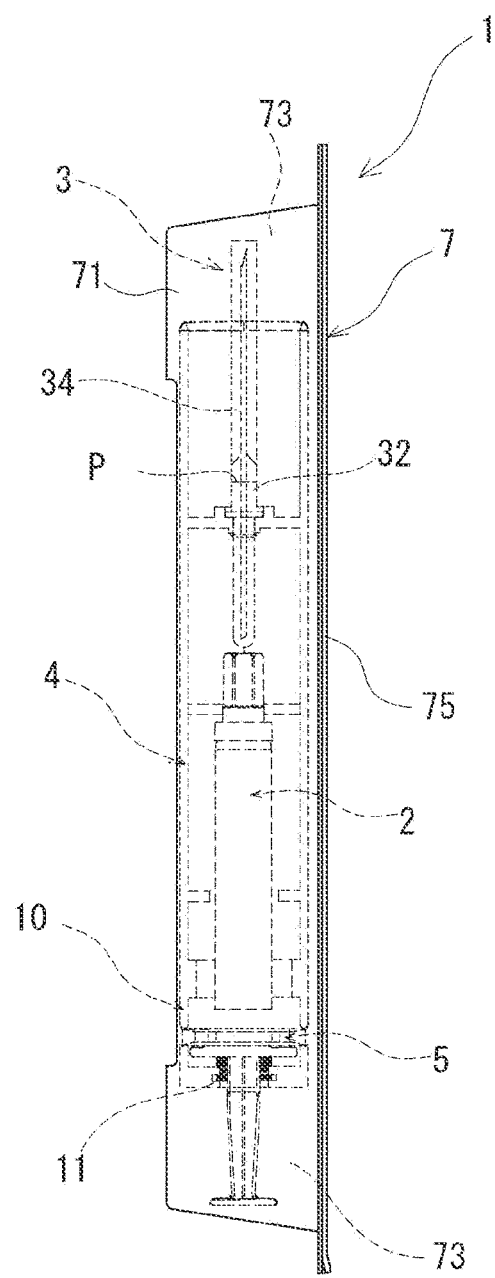
FIG. 2 is an explanatory view for describing the manufacturing method for the packaged medicine administration device according to the embodiment of the present invention.

In the embodiment illustrated in FIGS. 1 and 2, the package 7 includes a container main body 71 that accommodates the cylindrical case-encapsulated medicine administration device 10, and a sealing member 75 that seals an opening of the container main body 71 in an openable manner. In addition, the package may be a bag-shaped package that can be sealed and opened. Specific examples of the package include a blister packaging container and a soft bag-shaped packaging container. Note that as a form of the package, any form that can accommodate the cylindrical case-encapsulated medicine administration device 10 therein and can be sealed and opened may be used.

In the embodiment illustrated in FIGS. 1 and 2, the package 7 includes the container main body 71 having an accommodating recess 73 for accommodating the cylindrical case-encapsulated medicine administration device 10, and a peelable sealing film (sealing member) 75 for sealing an opening of the recess. The package 7 of the embodiment illustrated in FIGS. 1 and 2 is a blister package. Specifically, the container main body 71 of the package 7 includes the accommodating recess 73 and a flange forming portion 74 formed around the accommodating recess 73, and the sealing film 75 is peelably attached to the flange forming portion 74 of the container main body 71. In addition, the accommodating recess 73 of the container main body 71 has a shape such that the cylindrical case-encapsulated medicine administration device 10 does not easily move in the container main body.

Further, the hydrogen peroxide permeation amount adjustment functional package is used in the package 7 of this embodiment. The hydrogen peroxide permeation amount adjustment functional package refers to a package that allows and restricts permeation caused by diffusion of hydrogen peroxide. Specifically, it refers to one that allows permeation caused by diffusion of a hydrogen peroxide gas but suppresses permeation in a short time.

A hydrogen peroxide permeation function of the package can be evaluated by measuring a transpiration property of an aqueous solution containing hydrogen peroxide (a hydrogen peroxide solution). When the hydrogen peroxide solution is sealed in a package film and left under an environment of room temperature or higher, water and hydrogen peroxide gradually vaporize and fill the package film. In parallel with the vaporization and filling of the hydrogen peroxide, the hydrogen peroxide permeates and then passes through a package film body, and the degree thereof can be grasped from a decrease amount of hydrogen peroxide solution droplets in the package. That is, hydrogen peroxide solution droplets decrease and disappear in a short time in a porous film or the like through which hydrogen peroxide easily passes, but it takes a certain time for the hydrogen peroxide solution droplets to decrease and disappear in the package film that allows and restricts permeation caused by diffusion of hydrogen peroxide.

The package 7 preferably has a hydrogen peroxide permeation amount adjustment function in which a period during which hydrogen peroxide solution droplets disappear under conditions of 55° C. and 25% RH after a hydrogen peroxide solution adjusted to 300 mg/L is added as an amount of hydrogen peroxide per internal volume of the package and then the container is sealed is in a range of 3 hours to 72 hours. In particular, it is preferable to have a hydrogen peroxide solution droplet disappearance period (transpiration property) of 6 hours to 24 hours. Note that a container having the internal capacity of 0.2 mL per 1 cm 2 of the surface area of the package is assumed as the package here.

In addition, the package 7 may be any package having the hydrogen peroxide permeation amount adjustment function as a whole. That is, any of a combination in which only the container main body 71 has the hydrogen peroxide permeation amount adjustment function and the film 75 is impermeable to hydrogen peroxide, a combination in which only the film 75 has the hydrogen peroxide permeation amount adjustment function and the container main body 71 is impermeable to hydrogen peroxide, and a combination in which both the container main body 71 and the film 75 have the hydrogen peroxide permeation amount adjustment function may be used.

Furthermore, a material of the package is preferably one that is not easily degenerated by hydrogen peroxide. In addition, a waterproof material is preferably used as the material of the package.

Further, a material of the container main body 71 preferably has a certain degree of strength and hardness. In addition, the container main body 71 is preferably made of a material having low permeability to a hydrogen peroxide gas. As the material of the container main body 71, for example, polyolefin such as polypropylene and polyethylene, a vinyl chloride resin, a polyester resin, a polystyrene/polypropylene resin, polyethylene/ionomer (for example, ethylene-based, styrene-based, fluorine-based)/polyethylene, and the like can be suitably used, and in particular, low-density polyethylene/ionomer/low-density polyethylene is preferable from the viewpoint of the hydrogen peroxide permeation amount adjustment function.

Furthermore, a material having transparency is preferable among them. In addition, for example, in a case where the medicine stored in the syringe is easily affected by light, various pigments and ultraviolet absorbers may be contained in a material forming the container main body. Furthermore, it is preferable that the resin includes a layer having a thickness of about 30 μm to 70 μm and formed of a resin having low oxygen permeability and low water vapor permeability (for example, polyvinylidene chloride, an ethylene-vinyl alcohol copolymer, and polyethylene terephthalate). In addition, a resin including three layers of polyethylene terephthalate/ethylene-vinyl alcohol copolymer/polypropylene and a resin formed of polypropylene alone may be used.

Specifically, the sealing film 75 preferably has a film (base film) having low permeability to a hydrogen peroxide gas or substantially being impermeable to the hydrogen peroxide gas, and an adhesive resin layer fixed to at least an outer peripheral part of a lower surface of the film, and more preferably has a surface protective layer provided on an upper surface of the film. As the base film, a metal deposition film formed by depositing, on the surface thereof, a metal foil formed of aluminum, silver, gold or the like, or aluminum, silver, gold or the like, an inorganic material deposition film formed by depositing, on the surface thereof, $SiO_X$ or the like, or a gas barrier resin film such as a film formed of polyvinylidene chloride, polyvinylidene chloride-polyvinyl chloride, polyvinylidene chloride-acrylic acid ester copolymer, high density polyethylene or the like can be suitably used.

The adhesive resin layer is for peelably heat-sealing the base film and the container main body 71, and the following various peelable mechanisms can be used.

For example, when polypropylene is used for the heat-sealed surface of the container main body 71, as the adhesive resin layer, an ethylene-vinyl acetate resin, an ethylene-acrylic acid resin, an olefin resin such as a resin formed by blending polypropylene and polyethylene, a two-liquid curable urethane dry laminate adhesive, or the like can be suitably used.

In addition, when polyvinyl chloride is used as the container main body 71, as the adhesive resin layer, an olefin resin such as an ethylene-vinyl acetate resin or an ethylene-acrylic acid resin, a product obtained by blending a styrene-butadiene block copolymer with polystyrene, a vinyl chloride-vinyl acetate copolymer, a two-liquid curable urethane dry laminate adhesive, or the like can be suitably used.

Further, when polyester is used as the container main body 71, an olefin resin such as an ethylene-vinyl acetate resin or an ethylene-acrylic acid resin, a copolyester, or a two-liquid curable urethane dry laminate adhesive can be suitably used.

The surface protective layer is preferably formed by coating a synthetic resin, such as polyester such as PET, polypropylene, polyethylene, nylon, an epoxy resin, or a polyamide resin, or by bonding the synthetic resin film, paper, or the like. Further, the surface protective layer can also be used as a printing layer for describing necessary items such as a name, a filling amount, and a concentration of the medicine charged in the prefilled syringe of the cylindrical case-encapsulated medicine administration device 10. Note that a light-shielding material such as white ink may be interposed between the surface protective layer and the gas barrier film to form a light-shielding film.

Specific examples of the sealing film 75 may include a film including four layers such as polyethylene terephthalate/polyethylene/polyethylene terephthalate/adhesive resin or polyethylene terephthalate/ethylene-vinyl alcohol copolymer/stretched nylon/adhesive resin, and a film including three layers such as polyethylene terephthalate/stretched nylon/adhesive resin.

In addition, the hydrogen peroxide solution added in the manufacturing method is preferably 1.0 to 6.0 w/v %, and particularly preferably 2.0 to 4.0 w/v %. An addition amount (dropping amount) is 2 mg/L to 300 mg/L, preferably 15 to 100 mg/L as the amount of hydrogen peroxide per internal volume of the package. Specifically, it is preferable to add 0.01 mL to 0.10 mL of the hydrogen peroxide solution at 1.0 to 6.0 w/v % to 20 mL to 45 mL of the package. It is preferable to add 0.03 mL to 0.06 mL of the hydrogen peroxide solution at 2.0 to 4.0 w/v % to 20 mL to 45 mL of the package.

In addition, the hydrogen peroxide solution added in the manufacturing method may be 1.0 to 30.0 w/v %. Further, in a case where a hydrogen peroxide discharge period during which hydrogen peroxide is allowed to flow out of the package using the diffusion of hydrogen peroxide in the package (hereinafter, "hydrogen peroxide discharge period") is long [specifically, two and a half weeks (420 hours) or more, more specifically, three weeks (504 hours) or more], the hydrogen peroxide solution is preferably 3.0 to 30.0 w/v %, and particularly preferably 15 to 30 w/v %. In addition, when the hydrogen peroxide discharge period is not long [specifically, less than two and a half weeks, more specifically, two weeks (336 hours) or less], the hydrogen peroxide solution is preferably 1.0 to 6.0 w/v %, particularly 2.0 to 4.0 w/v % as described above. In addition, the addition amount (dropping amount) of the hydrogen peroxide solution may be 2 mg/L to 750 mg/L as the amount of hydrogen peroxide per the internal volume of the package. Further, when the hydrogen peroxide discharge period is long [specifically, two and a half weeks (420 hours) or more, more specifically, three weeks (504 hours) or more], the addition amount (dropping amount) of the hydrogen peroxide solution is preferably 6 to 750 mg/L, and particularly preferably 100 to 700 mg/L as the amount of hydrogen peroxide per the internal volume of the package. In addition, when the hydrogen peroxide discharge period is not long [specifically, less than two and a half weeks, more specifically, two weeks (336 hours) or less], the addition amount (dropping amount) of the hydrogen peroxide solution is preferably 2 to 300 mg/L, and particularly preferably 15 to 100 mg/L as the amount of hydrogen peroxide per the internal volume of the package.

Further, the addition of hydrogen peroxide may be performed by sealing the package 7 accommodating the cylindrical case-encapsulated medicine administration device 10 except for a part thereof, and adding the hydrogen peroxide solution from an unsealed site using a nozzle or the like.

Next, the step of sealing the package 7 accommodating the cylindrical case-encapsulated medicine administration device 10 is performed. This step is performed by sealing an unsealed portion of the package 7 accommodating the cylindrical case-encapsulated medicine administration device 10.

Specifically, as illustrated in FIGS. 1 and 2, the opening of the recess of the container main body 71 of the package 7 accommodating the cylindrical case-encapsulated medicine administration device 10 to which hydrogen peroxide has been added is sealed with the sealing film 75. The sealing is performed by sealing the flange forming portion 74 of the container main body 71 with the sealing film 75 by heat fusion, high-frequency fusion, or the like.

Next, in a state in which the package 7 is sealed, the package sealing and post-storage step of sterilizing the cylindrical case-encapsulated medicine administration device 10 with a hydrogen peroxide atmosphere formed by the added hydrogen peroxide is performed.

Further, in the package sealing and post-storage step, it is preferable to perform sterilization of the cylindrical case-encapsulated medicine administration device with the hydrogen peroxide atmosphere and hydrogen peroxide discharge for causing hydrogen peroxide to flow out from the inside of the package using diffusion of hydrogen peroxide of the package.

In the package sealing and post-storage step, the package 7, hermetically sealed and accommodating the cylindrical case-encapsulated medicine administration device 10, is placed under a condition that the hydrogen peroxide solution is gasified. Specifically, the gasification is performed under a temperature environment in which the hydrogen peroxide solution is gasified. In general, the gasification can be performed by maintaining a room-temperature state, but a heating state is maintained in the severe cold. Further, as the gasification of the hydrogen peroxide solution proceeds, the concentration of the hydrogen peroxide atmosphere in the package reaches a concentration at which a contact portion can be sterilized.

Note that the package 7 has low permeability or poor permeability to hydrogen peroxide, and permeation caused by diffusion of hydrogen peroxide from the package also occurs, but a gasification rate is faster. Thus, the concentration of the hydrogen peroxide atmosphere at which the cylindrical case-encapsulated medicine administration device 10 can be sterilized is reached inside the package, and the concentration further increases to reach the highest concentration when or slightly before the entire hydrogen peroxide is gasified, and the sterilization proceeds.

In this embodiment, the package having the hydrogen peroxide permeation amount adjustment function is used, after the highest concentration is reached, the hydrogen peroxide gradually flows out from the package according to the hydrogen peroxide permeation capacity of the package, but an outflow rate is slow. Further, due to the outflow of the hydrogen peroxide, the concentration in the package eventually becomes lower than the concentration of the hydrogen peroxide atmosphere at which the cylindrical case-encapsulated medicine administration device 10 can be sterilized. A period from the time when the concentration of the hydrogen peroxide atmosphere in the package reaches the concentration of the hydrogen peroxide atmosphere at which the outer surface can be sterilized to the time when the concentration of the hydrogen peroxide atmosphere becomes lower than the concentration of the hydrogen peroxide atmosphere at which the outer surface can be sterilized is a high-concentration atmosphere period, which is an effective sterilization period of the cylindrical case-encapsulated medicine administration device 10. The high-concentration atmosphere period is preferably about 14 days immediately after the sealing of hydrogen peroxide, and particularly preferably about 7 days immediately after encapsulation of hydrogen peroxide.

In addition, the lowest concentration in the high-concentration atmosphere period is preferably 0.05 mg/L to 2.0 mg/L, and particularly preferably 0.5 mg/L to 1.0 mg/L. In addition, the highest concentration in the high-concentration atmosphere period is preferably 10 mg/L to 300 mg/L, and particularly preferably 50 mg/L to 100 mg/L.

In addition, the lowest concentration in the high-concentration atmosphere period is preferably 0.05 mg/L to 10 mg/L. Further, when the above-described hydrogen peroxide discharge period is long [specifically, two and a half weeks (420 hours) or more, more specifically, three weeks (504 hours) or more], the lowest concentration in the high-concentration atmosphere period is preferably 0.15 mg/L to 10 mg/L, and particularly preferably 2.5 mg/L to 5.0 mg/L. In addition, when the hydrogen peroxide discharge period is not long [specifically, less than two and a half weeks, more specifically, two weeks (336 hours) or less], the lowest concentration in the high-concentration atmosphere period is preferably 0.05 mg/L to 2.0 mg/L, and particularly preferably 0.5 mg/L to 1.0 mg/L.

In addition, the highest concentration in the high-concentration atmosphere period is preferably 10 mg/L to 750 mg/L. Further, when the hydrogen peroxide discharge period is long [specifically, two and a half weeks (420 hours) or more, more specifically, three weeks (504 hours) or more], the highest concentration in the high-concentration atmosphere period is preferably 30 mg/L to 750 mg/L, and particularly preferably 375 mg/L to 700 mg/L. In addition, when the hydrogen peroxide discharge period is long [specifically, less than two and a half weeks, more specifically, two weeks (336 hours) or less], the highest concentration in the high-concentration atmosphere period is preferably 10 mg/L to 300 mg/L, and particularly preferably 50 mg/L to 100 mg/L.

In addition, it is preferable to change the atmosphere in the package by vertically inverting or swinging the sealed package during the high-concentration atmosphere period. In this manner, the contact of hydrogen peroxide with the cylindrical case-encapsulated medicine administration device 10 becomes more reliable. Specifically, this period is preferably performed at 1 to 30° C. In addition, the storage is preferably maintained at 10 to 80% RH, particularly 20 to 60% RH.

In addition, during this period, it is preferable to store the packaging container at an angle at which the inside is entirely filled with hydrogen peroxide, and it is particularly preferable to store the cylindrical case-encapsulated medicine administration device 10 in a horizontal state. With the storage in such a direction, the hydrogen peroxide gas spreads throughout the inside of the package, and thus, the inside of the package and the cylindrical case-encapsulated medicine administration device 10 are reliably sterilized. Note that the prefilled syringe may be stored in a vertical state. In addition, heating may be performed during this period. The heating is preferably performed at 30 to 100° C., particularly 40 to 80° C. The heating time is preferably 10 to 120 minutes, particularly 20 to 60 minutes.

Further, even after the concentration of the inside of the package becomes lower than the concentration of the hydrogen peroxide atmosphere at which the cylindrical case-encapsulated medicine administration device 10 can be sterilized, the outflow caused by the diffusion of hydrogen peroxide from the package continues, and almost all hydrogen peroxide flows out from the inside of the package 7. A period from the time when the concentration in the package becomes lower than the concentration of the hydrogen peroxide atmosphere at which the cylindrical case-encapsulated medicine administration device 10 can be sterilized to the time when the concentration of hydrogen peroxide in the package reaches a permissible residual concentration is the hydrogen peroxide discharge period. The hydrogen peroxide discharge period is preferably about 8 hours to 28 days although it differs depending on a hydrogen peroxide permeation rate of the package and the temperature and humidity during the storage. In particular, 1 day to 7 days are preferable. In addition, the above-described permissible residual concentration of the concentration of hydrogen peroxide is preferably 0.05 ppm or less. In addition, during the hydrogen peroxide discharge period, the packaged cylindrical case-encapsulated medicine administration device may be transported to a use site.

In addition, in a case where the cylindrical case-encapsulated medicine administration device uses a medicine or the like that is easily affected by oxygen, a deoxidizing agent may be accommodated inside the package. As a result, oxygen in the sealed package is absorbed, and oxidation of the medicine is prevented. When hydrogen peroxide is sealed in a packaging material containing a deoxidizing agent, decomposition of the hydrogen peroxide by the deoxidizing agent occurs, and thus, it is desirable to set the amount of hydrogen peroxide to be larger than that in a case where the deoxidizing agent is not added. In addition, the deoxidizing agent can decompose the sealed hydrogen peroxide at an early stage and prevent the hydrogen peroxide from remaining.

Figure 8:
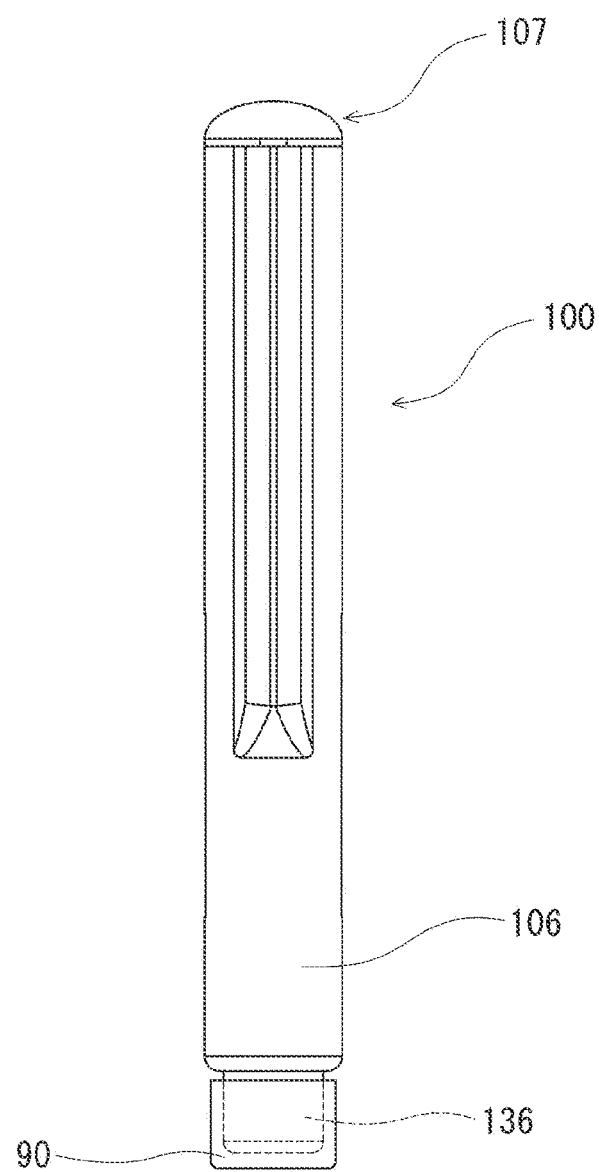
FIG. 8 is a front view of a cylindrical case-encapsulated medicine administration device used in a manufacturing method for a packaged medicine administration device according to another embodiment of the present invention.
Figure 9:
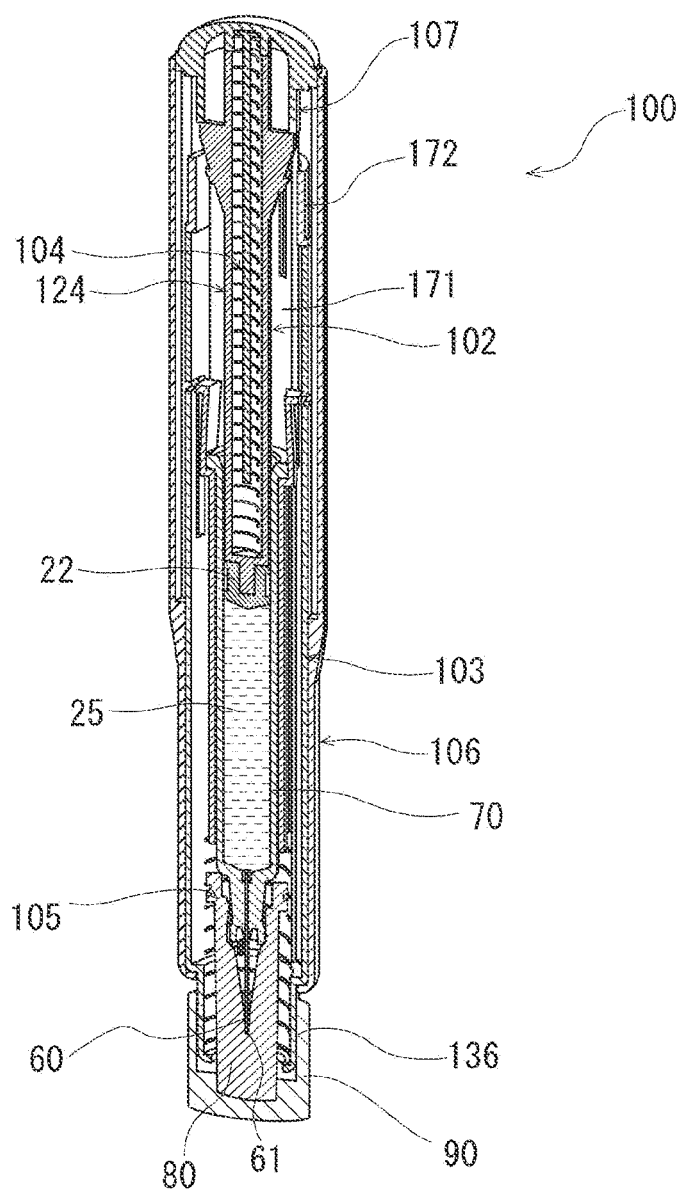
FIG. 9 is an explanatory view for describing an internal structure of the cylindrical case-encapsulated medicine administration device illustrated in FIG. 8.

In addition, the cylindrical case-encapsulated medicine administration device used in the present embodiment may be a cylindrical case-encapsulated medicine administration device 100 as illustrated in FIGS. 8 and 9.

The cylindrical case-encapsulated medicine administration device 100 includes: a prefilled syringe including an outer tube 70 with a puncture needle, a seal cap (puncture needle cap) 80 that seals a distal end portion of a puncture needle 60 of the outer tube 70, a slidable gasket 22 accommodated in the outer tube, and a medicine 25 charged in the outer tube 70; and an auto-injector mechanism that is accommodated in a cylindrical case, has a biasing member for pressing the gasket, and is mounted with the prefilled syringe.

The cylindrical case-encapsulated medicine administration device 100 of this embodiment includes the auto-injector and the above-described prefilled syringe mounted to the auto-injector.

Further, the auto-injector of the cylindrical case-encapsulated medicine administration device 100 includes a cylindrical case 106, a gasket pressing means 102 accommodated in the cylindrical case 106, a protector 103 accommodating the prefilled syringe, and a restricting means 107 for restricting movement of the gasket pressing means 102.

Further, the cylindrical case-encapsulated medicine administration device 100 can have an injection needle accommodation state (a first state) in which the protector 103 accommodates a needle tip 61 of the puncture needle 60; an administration-enabled state (in other words, a liquid discharge preparation completion state or a second state) in which the needle tip 61 protrudes from the protector 103 as the cylindrical case 106 moves to a distal end side and the gasket 22 is movable in the distal direction by the gasket pressing means 102; an administration state (in other words, a liquid discharge state or a third state) in which the gasket 22 moves in the distal direction by being pressed by the gasket pressing means 102 and the medicine 25 is discharged from the puncture needle 60; and an injection needle re-accommodation state (a fourth state) in which the cylindrical case 106 moves to a proximal end side and the needle tip 61 of the puncture needle 60 is accommodated in the protector 103.

In addition, the cylindrical case-encapsulated medicine administration device 100 includes a puncture needle cap 80 mounted to the outer tube 70 with a puncture needle. The needle tip 61 of the puncture needle 60 is inserted into the puncture needle cap 80.

Furthermore, the cylindrical case-encapsulated medicine administration device 100 includes a distal end cap 90 mounted to a distal end portion of the cylindrical case 106. The distal end cap 90 holds the puncture needle cap 80. Therefore, when the distal end cap 90 is detached from the cylindrical case 106, the puncture needle cap 80 is detached from the outer tube 70 with a puncture needle together with the distal end cap 90.

In such a cylindrical case-encapsulated medicine administration device 100, a step of adding hydrogen peroxide to a site inside the cylindrical case 106 is preferably performed by preparing the cylindrical case-encapsulated medicine administration device 100 in a state in which only the distal end cap 90 is not mounted, adding hydrogen peroxide to the inner side of the distal end cap 90, and mounting the distal end cap 90 to the cylindrical case 106. Furthermore, it is preferable to add the hydrogen peroxide to an outer surface of the cylindrical case-encapsulated medicine administration device 100 before and after the arrangement in a package.

Further, in the cylindrical case-encapsulated medicine administration device 100 of this embodiment, the puncture needle cap 80 is removed together with the distal end cap 90 at the time of use. In this state (from FIG. 9, the puncture needle cap 80 is in a state in which the distal end cap 90 is removed), the entire puncture needle 60 including the needle tip 61 is accommodated in the protector 103 forming a distal end portion of the cylindrical case-encapsulated medicine administration device 100. The needle tip 61 is located in a cylindrical distal end portion 136 of the protector 103.

Further, the cylindrical distal end portion 136 of the cylindrical case-encapsulated medicine administration device 100 is pressed against an administration target site, and the cylindrical case 106 is pressed toward the administration target site with a force exceeding the biasing force of the second biasing member 105, whereby the cylindrical case 106 moves toward the distal end side. In other words, when viewed from the entire cylindrical case-encapsulated medicine administration device, the protector 103 relatively retracts in the proximal direction. As a result, the cylindrical case 106 and the first restricting member 171, the gasket pressing means 102, and the prefilled syringe, which are fixed thereto move forward, and the puncture needle 60 protrudes and punctures the administration target site.

At the same time, restriction of movement of a gasket pressing member 124 by a second restricting member 172 is released, the gasket pressing member 124 is pressed by the first biasing member 104 to move forward and press the gasket 4, and the medicine 25 in the prefilled syringe passes through the puncture needle 60 and is injected into a living body.

Further, after administration is completed, the pressing of the cylindrical case 106 against a puncture target site is released so that the syringe is pushed back by the second biasing member 105 and moves to the proximal end side. As a result, the puncture needle 60 is accommodated again in the protector 103.

A manufacturing method for a packaged medicine administration device according to an embodiment of the present disclosure is a manufacturing method for a packaged medicine administration device including: a medicine administration device including an outer tube filled with a medicine and a puncture needle for medicine administration; a cylindrical case encapsulating and holding the medicine administration device; and a sealed package that accommodates the cylindrical case-encapsulated medicine administration device encapsulated and held by the cylindrical case.

A manufacturing method for a packaged medicine administration device according to an embodiment of the present disclosure includes: a step of preparing the cylindrical case-encapsulated medicine administration device; a step of adding hydrogen peroxide to a site to be located on the inner side of the cylindrical case of the cylindrical case-encapsulated medicine administration device; a step of accommodating the cylindrical case-encapsulated medicine administration device in the package; a step of sealing the package accommodating the cylindrical case-encapsulated medicine administration device; and a package sealing and post-storage step of sterilizing the cylindrical case-encapsulated medicine administration device with a hydrogen peroxide atmosphere formed by the added hydrogen peroxide in a state in which the package is sealed.

Therefore, in the package sealing and post-storage step, the package is filled with a hydrogen peroxide gas due to the added hydrogen peroxide, and the inside and an outer surface of the cylindrical case-encapsulated medicine administration device are sterilized by the filling hydrogen peroxide gas. Further, because the package is already packaged, a sterile state is maintained until the package is opened after the package sealing and post-storage step, and thus, it is possible to use the package in a highly microbially controlled atmosphere such as an operating room or an ICU.

A manufacturing method for a packaged medicine administration device according to an embodiment of the present disclosure is configured as follows.

(1) A manufacturing method for a packaged medicine administration device,
the packaged medicine administration device including: a medicine administration device including an outer tube filled with a medicine and a puncture device for medicine administration; a cylindrical case encapsulating and holding the medicine administration device; and a package accommodating the cylindrical case-encapsulated medicine administration device encapsulated and held by the cylindrical case and being sealed,
the manufacturing method including:
a step of preparing the cylindrical case-encapsulated medicine administration device;
a step of adding hydrogen peroxide to a site to be located on an inner side of the cylindrical case of the cylindrical case-encapsulated medicine administration device;
a step of accommodating the cylindrical case-encapsulated medicine administration device in the package;

a step of sealing the package accommodating the cylindrical case-encapsulated medicine administration device; and a package sealing and post-storage step of sterilizing the cylindrical case-encapsulated medicine administration device with an hydrogen peroxide atmosphere formed by the added hydrogen peroxide in a state in which the package is sealed.

This manufacturing method for a packaged medicine administration device is a manufacturing method for a packaged medicine administration device including: a medicine administration device including an outer tube filled with a medicine and a puncture needle for medicine administration; a cylindrical case encapsulating and holding the medicine administration device; and a sealed package that accommodates the cylindrical case-encapsulated medicine administration device encapsulated and held by the cylindrical case.

This manufacturing method for a packaged medicine administration device includes: a step of preparing the cylindrical case-encapsulated medicine administration device; a step of adding hydrogen peroxide to a site to be located on the inner side of the cylindrical case of the cylindrical case-encapsulated medicine administration device; a step of accommodating the cylindrical case-encapsulated medicine administration device in the package; a step of sealing the package accommodating the cylindrical case-encapsulated medicine administration device; and a package sealing and post-storage step of sterilizing the cylindrical case-encapsulated medicine administration device with a hydrogen peroxide atmosphere formed by the added hydrogen peroxide in a state in which the package is sealed.

Therefore, in the package sealing and post-storage step, the package is filled with a hydrogen peroxide gas due to the added hydrogen peroxide, and the inside and an outer surface of the cylindrical case-encapsulated medicine administration device are sterilized by the filling hydrogen peroxide gas. Further, because the package is already packaged, a sterile state is maintained until the package is opened after the package sealing and post-storage step, and thus, it is possible to use the package in a highly microbially controlled atmosphere such as an operating room or an ICU.

In addition, the above embodiment may be configured as follows.
(2) The manufacturing method for the packaged medicine administration device according to (1), wherein the package is a hydrogen peroxide permeation amount adjustment functional package that allows and restricts permeation caused by diffusion of the hydrogen peroxide.
(3) The manufacturing method for the packaged medicine administration device according to (2), in which, in the package sealing and post-storage step, the cylindrical case-encapsulated medicine administration device is sterilized with the hydrogen peroxide atmosphere and hydrogen peroxide discharge is performed to cause the hydrogen peroxide to flow out from the package using the diffusion of the hydrogen peroxide in the package.
(4) The manufacturing method for the packaged medicine administration device according to (2) or (3), in which the hydrogen peroxide permeation amount adjustment functional package is obtained by dropping 300 mg/L of hydrogen peroxide solution per internal volume of the package and sealing the package in such a manner that a period during which the dropped and added hydrogen peroxide solution disappears under conditions of 55° C. and 25% RH is in a range of 3 hours to 72 hours.
(5) The manufacturing method for the packaged medicine administration device according to any one of (1) to (4), in which the cylindrical case-encapsulated medicine administration device is capable of administering the medicine in a state of being encapsulated and held by the cylindrical case.
(6) The manufacturing method for the packaged medicine administration device according to any one of (1) to (5), in which
the cylindrical case-encapsulated medicine administration device includes a prefilled syringe and a puncture device that is mounted to the prefilled syringe at the time of use,
the puncture device includes: a hollow cylindrical member having a puncture needle portion on one end side and a connection needle portion on another end side; a hub arranged between the puncture needle portion and the connection needle portion of the hollow cylindrical member; and a puncture needle portion cap mounted on a side closer to the puncture needle portion of the hub,
the prefilled syringe includes: the outer tube; a gasket slidably accommodated in the outer tube; a distal end sealing member that seals a distal end of the outer tube and through which the connection needle portion is pierceable; the medicine with which the outer tube is filled; and a plunger that presses the gasket, and
the addition of hydrogen peroxide in the step of adding the hydrogen peroxide is performed by adding the hydrogen peroxide to a portion between the puncture needle portion cap and the hub.
(7) The manufacturing method for the packaged medicine administration device according to (6), in which
the cylindrical case-encapsulated medicine administration device includes a biasing member that abuts on the outer tube and biases the prefilled syringe toward the connection needle portion, and a stopper that is detachably inserted into a side portion opening of the cylindrical case, abuts on an outer surface protruding portion of the outer tube, and restricts movement of the prefilled syringe toward the hollow cylindrical member, and
in the medicine administration device, after the stopper is detached, the prefilled syringe moves toward the hollow cylindrical member by being pressed by the biasing member, and the sealing member of the prefilled syringe is penetrated by the connection needle portion.
(8) The manufacturing method for the packaged medicine administration device according to any one of (1) to (5), in which the cylindrical case-encapsulated medicine administration device includes: a prefilled syringe including an outer tube with a puncture needle, a seal cap that seals a distal end portion of the puncture needle of the outer tube, a slidable gasket accommodated in the outer tube, and a medicine with which the outer tube is filled; and an auto-injector mechanism that is accommodated in the cylindrical case, has a biasing member for pressing the gasket, and is mounted with the prefilled syringe.

The invention claimed is:
1. A manufacturing method for a packaged medicine administration device that comprises a medicine administration device comprising an outer tube filled with a medicine, and a puncture device for medicine administration; a cylindrical case encapsulating and holding the medicine administration device; and a package accommodating the cylindrical case-encapsulated medicine administration device encapsulated and held by the cylindrical case, the package being sealed, the manufacturing method comprising:
- a step of preparing the cylindrical case-encapsulated medicine administration device;
- a step of adding hydrogen peroxide to a site to be located on an inner side of the cylindrical case of the cylindrical case-encapsulated medicine administration device;
- a step of accommodating the cylindrical case-encapsulated medicine administration device in the package;
- a step of sealing the package accommodating the cylindrical case-encapsulated medicine administration device; and
- a step of sterilizing the cylindrical case-encapsulated medicine administration device with a hydrogen peroxide atmosphere formed by the added hydrogen peroxide in a state in which the package is sealed.

2. The manufacturing method for the packaged medicine administration device according to claim 1, wherein:
the package is a hydrogen peroxide permeation amount adjustment functional package.

3. The manufacturing method for the packaged medicine administration device according to claim 2, wherein, in the step of sterilizing, the cylindrical case-encapsulated medicine administration device is sterilized with the hydrogen peroxide atmosphere and hydrogen peroxide discharge is performed to cause the hydrogen peroxide to flow out from the package using diffusion of the hydrogen peroxide in the package.

4. The manufacturing method for the packaged medicine administration device according to claim 2, wherein, the hydrogen peroxide permeation amount adjustment functional package is obtained by dropping 300 mg/L of hydrogen peroxide solution per internal volume of the package, and sealing the package in such a manner that a period during which the dropped and added hydrogen peroxide solution disappears under conditions of and 25% RH is in a range of 3 hours to 72 hours.

5. The manufacturing method for the packaged medicine administration device according to claim 1, wherein the cylindrical case-encapsulated medicine administration device is configured to administer the medicine in a state of being encapsulated and held by the cylindrical case.

6. The manufacturing method for the packaged medicine administration device according to claim 1, wherein:
the cylindrical case-encapsulated medicine administration device comprises a prefilled syringe, and a puncture device that is mounted to the prefilled syringe at a time of use,
the puncture device comprises:
- a hollow cylindrical member having a puncture needle portion on one end side and a connection needle portion on another end side,
- a hub located between the puncture needle portion and the connection needle portion of the hollow cylindrical member, and
- a puncture needle portion cap mounted on a side closer to the puncture needle portion of the hub, the prefilled syringe comprises:
- the outer tube,
- a gasket slidably accommodated in the outer tube,
- a distal end sealing member that seals a distal end of the outer tube and through which the connection needle portion is pierceable,
- the medicine with which the outer tube is filled, and
- a plunger configured to press the gasket, and the addition of hydrogen peroxide in the step of adding the hydrogen peroxide comprises adding the hydrogen peroxide to a portion between the puncture needle portion cap and the hub.

7. The manufacturing method for the packaged medicine administration device according to claim 6, wherein:
the cylindrical case-encapsulated medicine administration device comprises:
- a biasing member that abuts on the outer tube and biases the prefilled syringe toward the connection needle portion, and
- a stopper that is detachably inserted into a side portion opening of the cylindrical case, abuts on an outer surface protruding portion of the outer tube, and restricts movement of the prefilled syringe toward the hollow cylindrical member, and the medicine administration device is configured such that, after the stopper is detached, the prefilled syringe moves toward the hollow cylindrical member by being pressed by the biasing member, and the sealing member of the prefilled syringe is penetrated by the connection needle portion.

8. The manufacturing method for the packaged medicine administration device according to claim 1, wherein:
the cylindrical case-encapsulated medicine administration device comprises:
- a prefilled syringe comprising an outer tube with a puncture needle, a seal cap that seals a distal end portion of the puncture needle of the outer tube, a slidable gasket accommodated in the outer tube, and a medicine with which the outer tube is filled, and
- an auto-injector mechanism that is accommodated in the cylindrical case, has a biasing member configured to press the gasket, and is mounted with the prefilled syringe.

* * * * *